United States Patent [19]

Elwing

[11] 4,356,260

[45] Oct. 26, 1982

[54] ENZYMATIC INDICATOR SYSTEM

[76] Inventor: Hans B. Elwing, Chalmersgatan 5, 411 35 Gothenburg, Sweden

[21] Appl. No.: 252,473

[22] Filed: Apr. 9, 1981

Related U.S. Application Data

[63] Continuation of Ser. No. 143,939, Apr. 25, 1980, abandoned, which is a continuation of Ser. No. 23,191, Mar. 14, 1979, abandoned.

[30] Foreign Application Priority Data

Jul. 14, 1977 [SE] Sweden .............................. 7708179

[51] Int. Cl.³ .............................................. C12Q 1/02
[52] U.S. Cl. .......................................... 435/29; 435/4; 435/7; 435/30; 23/230 B
[58] Field of Search ................. 23/230 B; 204/180 R, 204/180 G; 422/57; 435/4, 7, 29, 30, 288, 291

[56] References Cited

U.S. PATENT DOCUMENTS

| | | | |
|---|---|---|---|
| 3,401,087 | 9/1968 | Kuzel | 435/29 |
| 3,730,843 | 5/1973 | McKie | 435/23 |
| 3,905,767 | 9/1975 | Morris et al. | 422/57 |
| 3,917,515 | 11/1975 | Goldberg | 435/288 |
| 4,066,512 | 1/1978 | Lai et al. | 435/4 |
| 4,169,765 | 10/1979 | Keyes | 435/291 |
| 4,234,683 | 11/1980 | McMillan | 435/29 |

FOREIGN PATENT DOCUMENTS 360177 9/1973 Sweden .
1320086 6/1973 United Kingdom ................... 435/4

OTHER PUBLICATIONS

Webster, "Deoxyribonuclease: A Sensitive Assay Using Radial Diff. in Agarose Containing Methyl--Green-DNA Complex", *Biochem. Biophys. Acta,* 247 (1971), pp. 54-61.
Chemical Abstracts, 77 (1972), 30705r.

*Primary Examiner*—Peter A. Hruskoci
*Attorney, Agent, or Firm*—Stevens, Davis, Miller & Mosher

[57] ABSTRACT

Method for the determination of enzymatic activity in which a sample is added to a well in or a defined surface of a liquid-saturated porous matrix covering a thin layer of a substance sensitive to enzymatic lysis deposited on the solid surface of a carrier. The sample is permitted to diffuse or migrate electrophoretically in the matrix and react with the substance sensitive to enzymatic lysis. The matrix is then removed whereon lysis can be indicated on the solid surface. The enzyme-containing sample can be a bacteria colony on the matrix. Plastic material is preferred for the solid surface.

6 Claims, No Drawings

ENZYMATIC INDICATOR SYSTEM

This is a continuation of application Ser. No. 143,939 filed Apr. 25, 1980, now abandoned, which in turn is a continuation of application Ser. No. 023,191 filed Mar. 14, 1979, now abandoned.

The present invention relates to an enzymatic indicator system based on a two-phase system, in which an enzyme substrate is bound to the surface of a solid phase and in which the presence and quantity of an enzyme capable of reacting with the compound bound to said surface is determined by permitting the enzyme to diffuse from a well in a liquid-saturated immobilized phase located on said surface. The presence and quantity of enzyme is then indicated on the solid phase in a suitable manner.

Enzymatic types of testing methods have a central position within the diagnostic techniques of medicine, microbiology and applied biochemistry in general. This is predominantly due to the fact that such methods afford the possibility of determining minute quantities of the specific reactants in question in complex systems.

Enzymatic test methods have been used in diagnosing various diseases by determining enzyme activity in serum, and other biological fluids, as well as enzyme activity generated by microorganisms.

These enzymatic tests are generally effected by various indicator systems involving colour changes, lysis of cells as erythrocytes, or degradation of molecules or the like.

The method according to the invention involves depositing a substrate on a solid surface as a thin layer of a substance sensitive to enzymatic lysis, whereafter there is placed on the thin layer an immobilized matrix in which the enzyme to be determined is permitted to diffuse or electrophoretically migrate during a measured period of time, whereafter the matrix is removed and the lysis reaction surface area on the solid surface is determined by adding an indicator substance, or in some other suitable way. The thin layer of said substance is suitably applied to the solid surface in the following manner: A liquid medium, suitably based on water, is first dispensed to the solid surface. A solution containing said substances is then added to the liquid medium to diffuse therein, whereafter the substance is permitted to deposit itself onto the solid surface, becoming bound to the solid surface with a force of such magnitude that said surface, subsequent to the aqueous medium having been removed, can be washed without the layer being removed therefrom.

The solid surface is suitably a transparent material, such as glass or a plastics material, e.g. polystyrene, polyacrylnitrile, polyolefines and copolymers thereof. It has been found in recent years, that plastics surfaces advantageously adsorb macro-molecules to form very uniform and reproduceable layers.

A technique for visualizing enzyme reactions is one in which a thin layer of indium particles is vapor-deposited on the solid surface. The enzyme reactions are carried out on the indium layer, whereafter the reactions can be observed as a light-propagation phenomena on the indium surface. The most serious disadvantages with this technique appear to be the requirement of advanced apparatus for producing a uniform and reproducable layer of indium on large surfaces. This restricts the rational use of such surfaces. Furthermore, it is difficult to classify in a reaction as a positive or a negative one in borderline cases, since this indicator system has a flat amplitude and the indication can only be judged subjectively.

Another much simpler technique for visualizing enzymatic reactions on solid surfaces is one employing the condensation of water vapor. This technique involves exposing the dried surface to vapor, whereupon it is possible to determine whether a reaction has taken place and the extent of any such reaction from the pattern formed by the condensation. The principles of this technique were described by Langmuir in 1936. This method is as sensitive as the method employing an indium layer, but has a steeper indication-amplitude. Moreover, it permits the objective analysis by contact-copying of the condensation pattern on the surfaces by irradiation of photographic paper and development thereof.

The indication of biological surface reactions is thus best effected with vapour condensation on the plastics surface (Vapour condensation on surface, VCS, see Adams, Klings, Fisher and Vroman, Journal of Immunological Methods, 3, (1973) pages 227–232), which, because of its simplicity, is the preferred method. Other known methods can also be used, such as the so-called ELISA-method (Enzyme-linked immunosorbent assay, J. Immun. 109:129 (1972), or particle adsorption technique, using a slurry of barium sulphate for example, and various colouring techniques.

The reason why it is possible to observe a change in the thin layer on the solid transparent surface as a result of vapour condensation is due to the fact that the so-called Zeta-potential or surface tension against water is changed on the surface when a reaction has taken place. In principle, all hydrophobic surfaces have a surface-tension angle of from 90° to 170°. Those plastics surfaces which normally have such properties include polystyrene, polyacrylonitrile, polyethylene and copolymers thereof.

The substance bound to the plastics surface is able to react selectively with a further substance, either on reacted parts or on unreacted parts of the substance, and the reaction in question can be shown visually in situ even when it is difficult to make the reaction directly visible on the substrate after the enzyme reaction.

An immobilized matrix through which the unknown substance shall diffuse is then applied to the surface having the antigen thereon. Such immobilized matrices are well known within the technique of analysis, and may comprise aqueous gels or various types of sediment or fibrous substances. The most conventional method is one in which a gel is used, in particular an agar gel, suitably comprising a buffered 1%-solution of agar which is permitted to solidify. A well is then formed in the matrix, there being supplied to the well a solution containing the unknown substance. The unknown substance may also be supplied in cellulose plates or the like, which have been saturated with the solution. The system is left at a suitable temperature of between 5° and 50° C., for the unknown substance to diffuse from the well.

Compared with previously known methods of obtaining quantitative measurements of minute quantities of biological materials, the novel method exhibits a simplicity which has not previously been achieved, and therewith a subsequent increase in capacity and decrease of costs. Thus, it is relatively simple to obtain uniform, thin component layers on plastics surfaces, the adhesion of the layer to the plastics surface being independent of the concentration of the substance forming the layer in the solution applied to the surface in a sufficient quantity, as compared to the adhesion forces obtained in respect of glass surfaces.

The method according to the invention is thus used for enzymatic analysis of substances sensitive thereto, the plastics surface having applied to it a thin layer of an enzyme substrate and an immobilized matrix over said substrate, whereafter an enzyme-containing sample quantity is applied to the matrix and permitted to diffuse therein; whereafter the matrix is removed and those parts of the enzyme substrate which have been affected by the enzyme are indicated by lysis being obtained in this region. The method is much simpler to carry out than known methods, the latter employing reactions in a mass and chromatographic systems. A high degree of sensitivity is achieved, which can be subscribed to the fact that a high substrate concentration is obtained in the thin layer. The method provides information concerning the diffusion properties of the enzyme, it being possible to determine the molecular weight from the diffusion rate, if the concentration and temperature are known at the same time. The method enables the extracellular enzyme activity of bacteria to be examined in a simple and reliable manner.

I claim:

1. A method of determining enzymatic activity comprising
    providing a solid surface,
    binding a thin layer of an indicator for lysis determination to said solid surface,
    applying an immobilized matrix to said thin layer,
    supplying a quantity of an enzyme-containing sample to said immobilized matrix,
    permitting the enzyme in said enzyme-containing sample to diffuse in said immobilized matrix and react with said thin layer,
    removing said immobilized matrix, and
    determining the lysis indicated on said solid surface.

2. The method of claim 1 wherein said enzyme-containing sample is a bacterial culture, and said immobilized matrix contains a nutrient for bacterial growth, thus causing the growth of extra cellular enzymes on the surface of said immobilized matrix, said extra cellular enzymes diffusing through said immobilized matrix.

3. The method of claim 1, wherein said surface is a plastics material selected from the group consisting of polystyrene, polyacrylonitrile, polyolefines, and copolymers thereof.

4. A method of determining enzymatic activity comprising
    providing a solid surface,
    binding a thin layer of an indicator for lysis determination to said solid surface,
    applying an immobilized matrix to said thin layer,
    supplying a quantity of an enzyme-containing sample to said immobilized matrix,
    permitting the enzyme in said enzyme-containing sample to migrate electrophoretically in said immobilized matrix and react with said thin layer,
    removing said immobilized matrix, and
    determining the lysis indicated on said solid surface.

5. The method of claim 4 wherein said enzyme-containing sample is a bacterial culture, and said immobilized matrix contains a nutrient for bacterial growth, thus causing the growth of extra cellular enzymes on the surface of said immobilized matrix, said extra cellular enzymes migrating through said immobilized matrix.

6. The method of claim 4 wherein said surface is a plastics material selected from the group consisting of polystyrene, polyacrylonitrile, polyolefines, and copolymers thereof.

* * * * *